United States Patent

Yankielun

[11] Patent Number: 5,861,756
[45] Date of Patent: Jan. 19, 1999

[54] METHOD OF DETECTING ACCRETION OF FRAZIL ICE ON WATER

[76] Inventor: Norbert E. Yankielun, 54 Nottingham Cir., Lebanon, N.H. 03766

[21] Appl. No.: 929,254

[22] Filed: Sep. 15, 1997

[51] Int. Cl.⁶ .................................................. G01N 27/22
[52] U.S. Cl. .................. 324/667; 324/664; 324/681; 324/689; 324/690; 73/170.26; 340/580
[58] Field of Search ..................... 324/663, 664, 324/667, 668, 671, 672, 674, 681, 682, 686, 687, 689, 690; 73/170.26; 340/580

[56] References Cited

U.S. PATENT DOCUMENTS

| | | | |
|---|---|---|---|
| 2,133,483 | 10/1938 | Shaw | 324/664 |
| 3,078,709 | 2/1963 | Clark | 73/61.41 |
| 3,242,473 | 3/1966 | Shivers, Jr. et al. | 340/580 |
| 3,696,360 | 10/1972 | Gajewski | 324/696 |
| 3,873,927 | 3/1975 | Overall | 324/667 |
| 3,882,381 | 5/1975 | Gregory | 324/667 |
| 4,135,151 | 1/1979 | Rogers et al. | 324/687 |
| 4,281,286 | 7/1981 | Briggs | 324/687 |
| 4,347,709 | 9/1982 | Wu et al. | 340/580 |
| 4,745,803 | 5/1988 | Haavasoja | 340/580 |
| 4,766,369 | 8/1988 | Weinstein | 324/671 |
| 5,062,120 | 10/1991 | Daly et al. | 374/143 |
| 5,125,265 | 6/1992 | O'Connell et al. | 324/664 |
| 5,134,380 | 7/1992 | Jonas | 324/674 |
| 5,389,884 | 2/1995 | Nakamura et al. | 324/663 |
| 5,398,547 | 3/1995 | Gerardi et al. | 324/671 |
| 5,551,288 | 9/1996 | Geraldi et al. | 324/671 |
| 5,569,850 | 10/1996 | Rauckhorst, III | 73/170.26 |

*Primary Examiner*—Diep N. Do
*Attorney, Agent, or Firm*—Luther A. Marsh

[57] ABSTRACT

The spaced plates of a capacitor are immersed in water adjacent water intake grating so that water flowing toward the grating passes between and in contact with the plates so that frazil ice may accrete on the facing surfaces of the plates. As accretion occurs, the capacitance changes to indicate the amount of accretion of frazil ice which is detected thereby providing an indication of the amount of accretion of frazil ice on the grating.

6 Claims, 3 Drawing Sheets

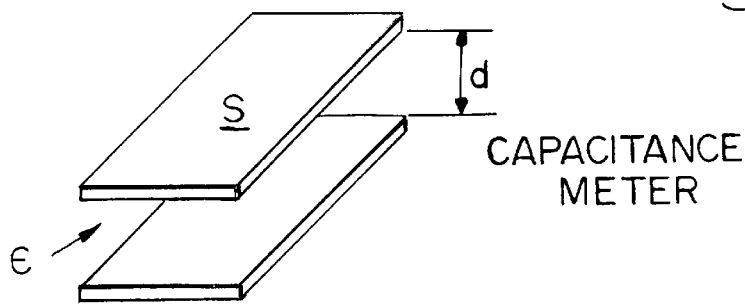
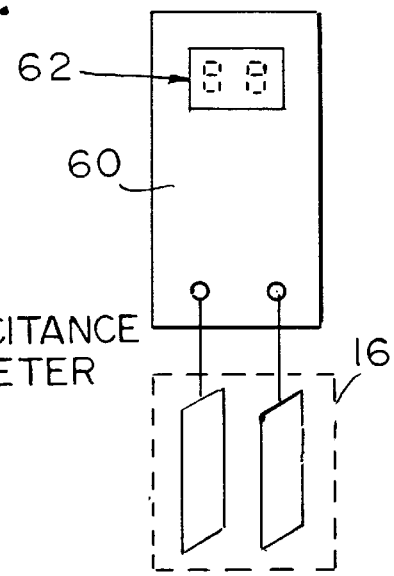
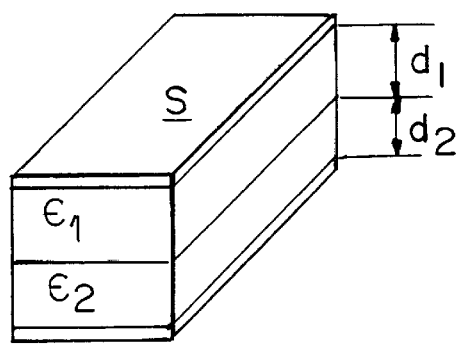
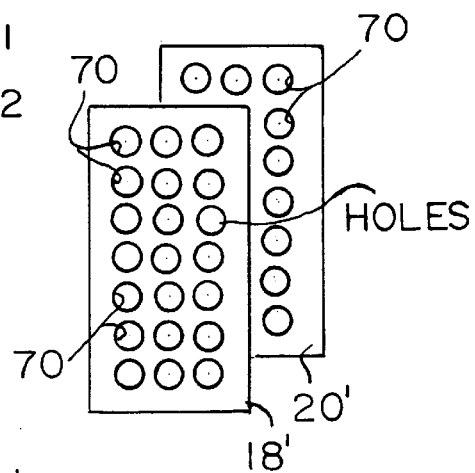
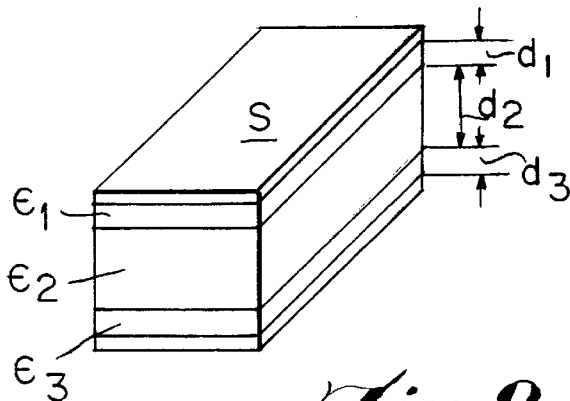
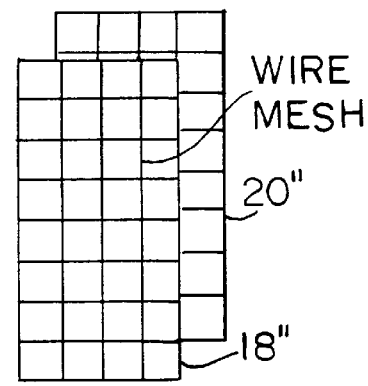

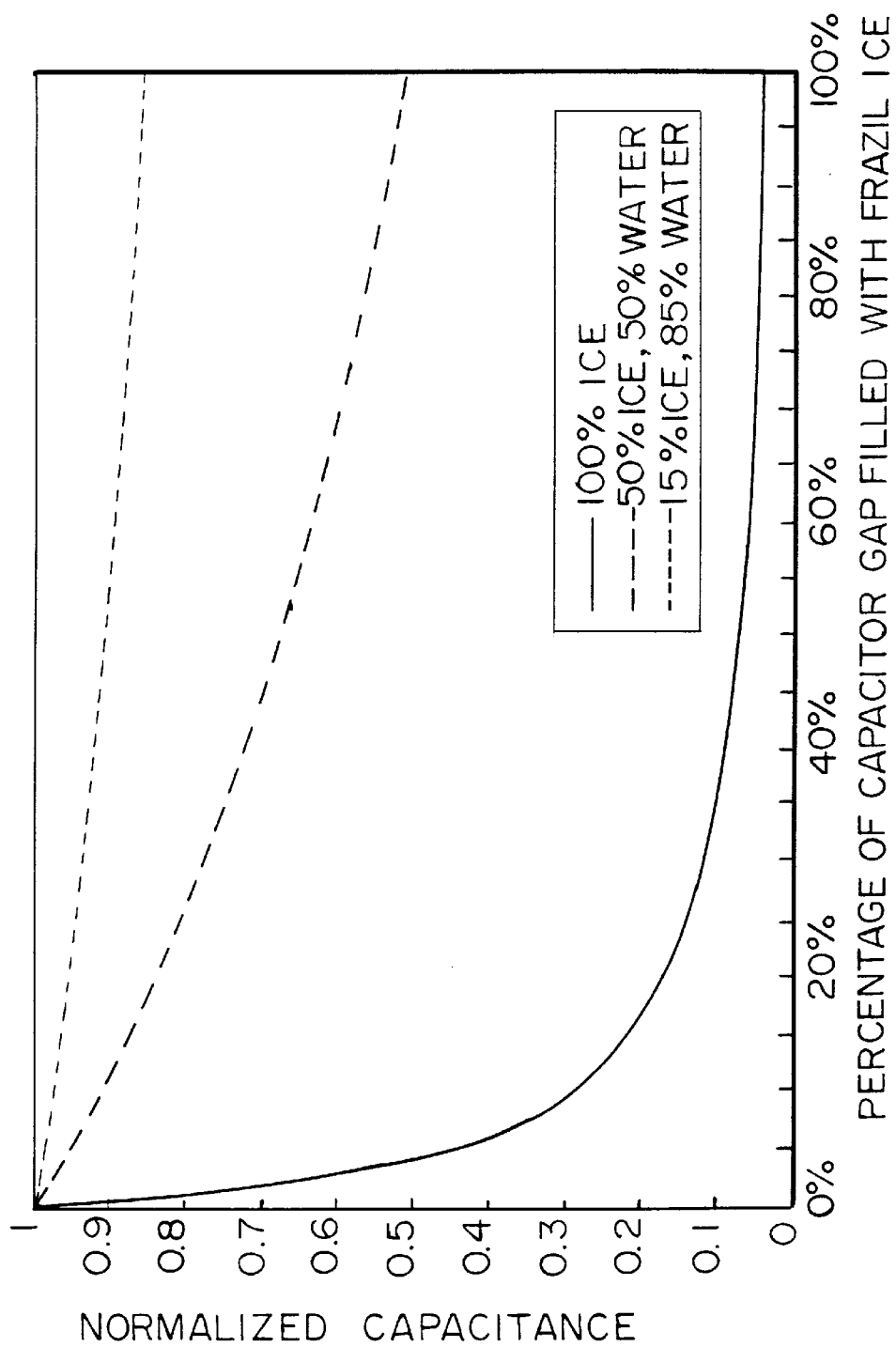

METHOD OF DETECTING ACCRETION OF FRAZIL ICE ON WATER

BACKGROUND OF THE INVENTION

Industrial, commercial and municipal facilities located in regions that are subject to seasonal freezing and are required to draw quantities of water from rivers during the freezing season are subject to the negative effects of the buildup of frazil ice on gratings protecting water intakes from the ingestion of foreign objects and aquatic life. These negative effects can include, depending on the nature of the plant in question, lower operating efficiencies, loss of cooling water, damage to pump components, and loss of revenues due to unexpected down time.

Currently, the only detection and alarm systems in implementation consists of complex, mechanical systems with moving components that have low reliability and require significant maintenance.

Such a mechanical system is shown, for example, in U.S. Pat. No. 5,062,120. In contrast, it is an objective of the present invention to provide a simple, economical, reliable and low maintenance system for detecting and indicating the occurrence of the accretion of frazil ice on water intake gratings.

Frazil ice is formed when turbulent water is cooled. Once the water is supercooled a few hundredths of a degree, minute ice crystals form in the water and conglomerate, resulting in flocks of frazil ice. Frazil forms mainly in rivers but has been seen in lakes, cooling ponds and in the ocean where the surface is turbulent and there is ambient cooling. Many water intakes for power generation plants and other industrial and commercial processing plants have waterway approaches that have turbulent flow, a prime condition for the formation of frazil ice. As long as the water temperature is at or below freezing, it is possible for frazil ice to form. Once formed, frazil ice will adhere to, and continue to accrete on, practically any natural or man-made object in the water, including: rocks, wood, and metal structures (including protective gratings over water intakes known in the industry as "trash racks"). Under certain frazil growth conditions, trash racks on water intakes have been known, without warning, to completely occlude in a matter of a few hours.

SUMMARY OF THE INVENTION

This invention exploits the difference in the dielectric constants of ice and water and the change in electrical capacitance between two metallic plates that occurs when the dielectric constant of material in the space between the plates changes. In water where conditions are favorable for the growth of frazil ice, accretion will occur on the plates of an immersed capacitor. As the accretion of ice thickens on the capacitor plates, there is a measurable decrease in the capacitance. This change in capacitance can be electronically detected and used to indicate the presence of frazil ice. An alarm may be sounded to alert operating personnel of the problem.

A capacitor including spaced conductive plates is immersed in water adjacent the water intake grating of a facility requiring the intake of water in a geographical region where frazil ice formation occurs. The capacitor is positioned so that water flowing toward the grating passes between and in contact with the plates of the capacitor such that frazil ice may accrete on the facing surfaces of the plates. As frazil ice accretes on the plate surfaces, the capacitance of the capacitor changes thereby indicating the amount of accretion of frazil ice on the capacitor, which is similar to the amount of frazil ice which has accreted on the adjacent grating. The changes in capacitance of the capacitor are detected to indicate the amount of accretion of frazil ice.

The invention provides real-time monitoring/alarming of frazil ice buildup on water intake grating. The monitoring can be carried out at a remote location several thousand feet from the capacitor sensor. The sensor and signal processing electronics can be co-located, if desired. An alarm can be telemetered via telephone line or narrow-band radio link. The invention has no moving mechanical components, but rather employ simplified electronics easy to install. The invention requires low maintenance and there is minimum user interface.

The invention may be used to improve plant operation, efficiency and maintenance in numerous industrial, commercial, and municipal operations such as hydroelectric power plant water intake grates, fossil-fueled and nuclear-fueled power plants requiring cooling water, industry/manufacturing plants requiring cooling water, water supply plants, snow-making water pumping equipment and in scientific studies including the measurement of frazil growth pertaining to river hydraulics.

DESCRIPTION OF THE DRAWINGS

FIG. 1 is a schematic view illustrating the theory involved in calculating the capacitance of a parallel-plate capacitor with a single layer of homogenous medium between the plates;

FIG. 2 is a view similar to FIG. 1 with two layers of different dielectric materials between the plates;

FIG. 3 is a view similar to FIG. 2 with three layers of dielectric material between the plates;

FIG. 4 is a graph illustrating the capacitance of the capacitor of the invention versus the percentage of the capacitor gap which is filled with frazil ice;

FIG. 6 is a schematic view of a modified form of the method of the invention;

FIG. 7 illustrates a modified form of the plates of the capacitor; and

FIG. 8 illustrates a further modified form of the plates of the capacitor.

THEORY OF OPERATION

Figure 5:
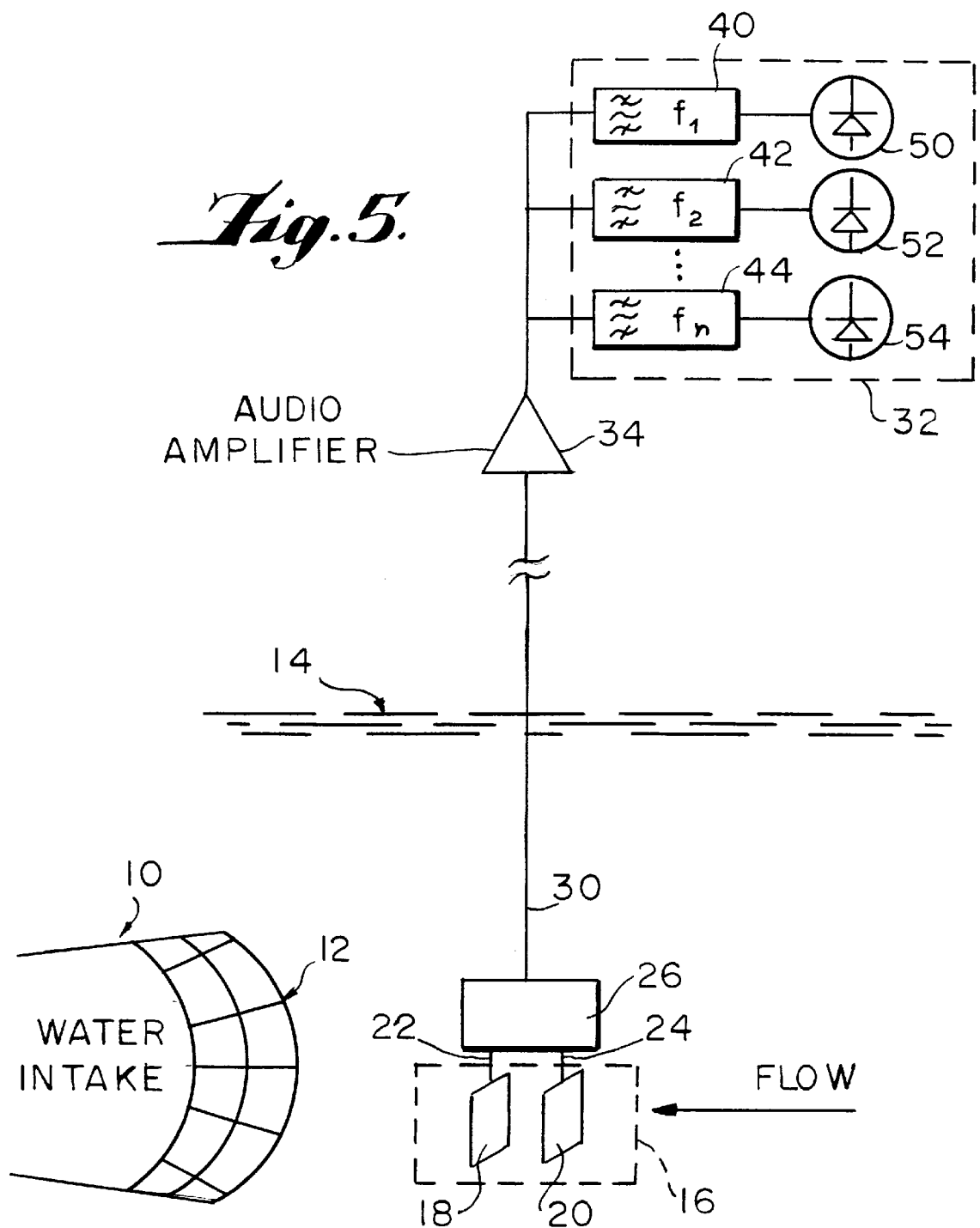
FIG. 5 is a schematic view illustrating the method of the invention.

The capacitance, C(pf) of a parallel-plate capacitor with a single layer of homogenous dielectric medium (FIG. 1) is calculated by:

$$C = \epsilon S / 11.3d \quad (1)$$

where:
$\epsilon$=dielectric constant of medium between capacitor plates
S=area of capacitor plates (cm$^2$)
d=distance between plates (cm)

The capacitance of a parallel-plate capacitor with two layers of different dielectric materials (FIG. 2) is given by:

$$C = 1/[11.3d_1/\epsilon_1 S) + 11.3d_2/\epsilon_2 S)] \quad (2)$$

where:
$\epsilon_1$=dielectric constant of first medium
$\epsilon_2$=dielectric constant of second medium
$d_1$=thickness of first dielectric medium (cm)

$d_2$=thickness of second dielectric medium (cm)

By simple extension, the formula can be modified to define the capacitance of a three-layered medium (FIG. 3), assuming that there is accretion of a layer frazil ice on each of the capacitor plates and a layer of water between:

$$C=1/[11.3d_1/\epsilon_1 S)+(11.3d_2/\epsilon_2 S)+(11.3d_3/\epsilon_3 S)] \quad (3)$$

where:
$\epsilon_3$=dielectric constant of third medium
$d_3$=thickness of third dielectric medium (cm)

If a capacitor with known dimensions of S and d is immersed in a bath of water ($\epsilon$=80), then the resulting value of capacitance can be calculated using Equation (1). If this capacitor is immersed in the water bath at or a few hundredths of a degree below 0° C., frazil ice starts to accrete on the plates. For the sake of illustration, a uniform coating on both plates is assumed; and the capacitance of the capacitor can be calculated using Equation (3). In practice, the frazil ice will accrete on the capacitor plates in a more random or irregular pattern causing changes in the capacitance which are more difficult to quantify. Nevertheless, for the detection of the presence of frazil ice, it is only essential to look for a decrease in capacitance from an initial value to below an experimentally determined level. Solid freshwater ice has an $\epsilon$ of 3.7. Frazil ice, a mixture of liquid water and ice, will have an $\epsilon$ that is somewhere between that of water and pure ice, depending on the percentages of the two components present.

FIG. 4 shows a graph of normalized results of a calculation using Equation (3), where the thickness of the accreting frazil goes from zero to 100% of the capacitor gap distance, d. The lines on the graph indicate different levels of ice/water consistency; the solid line representing an accretion of 100% ice on the capacitor plates, and the dashed lines representing the results of different ice/water mixture frazil accretions. The dielectric constant of freshwater ice is 3.7 and the dielectric constant of the 50%/50% ice/water mix was calculated to be approximately 41 using a linear volumetric mixing relationship.

DESCRIPTION OF THE PREFERRED EMBODIMENT

Referring to the drawings, there is shown in FIG. 5 a conventional water intake 10 having the usual protective trash rack or grating 12 over the inlet of the water intake to prevent undesirable material from being sucked into the intake. The surface of a body of water is indicated at 14. A capacitor 16 has a pair of spaced conductive plates 18 and 20 which include substantially parallel facing surfaces. The capacitor and its plates are immersed in the body of water below the surface 14 thereof. The capacitor and its plates are disposed adjacent the grating in such a location that water flowing toward the grating and the inlet of the water intake passes between the capacitor plates and in contact with facing surfaces of the plates.

Capacitor 16 is connected by leads 22 and 24 to an AC bridge as the capacitive element of an RC oscillator 26 which is connected by electrical cable 30 to detecting and indicating means 32. An audio amplifier 34 may be connected between the oscillator 26 and means 32, especially when the means 32 is disposed a substantial distance from the oscillator.

Sensor means 32 may include a plurality of band pass filters 40, 42 and 44 which are connected to light emitting diodes 50, 52 and 54 respectively. The band pass filters can be selected to pass signals of different frequencies to indicate changes in the capacitance of capacitor 16, thereby indicating different degrees of accretion of frazil ice on the capacitor plates. Diodes 50, 52 and 54 provide a visual indication which can be observed by operating personnel. It is apparent that suitable alarm means can be substituted for the diodes to alert personnel to the potential problems due to accretion of frazil ice.

Referring to FIG. 6, capacitor 16 may be connected to a conventional capacitance meter 60 providing a digital readout at 62 of changes in capacitance.

The initial value of the capacitance is noted and changes thereof can be monitored by an observer. The initial value of the capacitance can also be stored in the computer memory of a specially designed frazil ice detection and alarming system.

A thermo-couple or other temperature sensing device can be co-located with the capacitor to provide a check of the water temperature.

The plates of the capacitor may be of conventional construction, but are preferably of a construction which encourages frazil ice accretion. As seen in FIG. 7, capacitor plates 18' and 20' are formed of metal and have a plurality of holes 70 which are drilled or punched therethrough. As seen in FIG. 8, capacitor plates 18" and 20" are formed of wire mesh.

While there has been described what is considered to be the exemplary embodiment of the invention, it will be apparent to those skilled in the art the various changes and modifications that may be made therein without departing from the invention, and it is intended in the appended claims to cover such changes and modifications as fall within the true spirit and scope of the invention.

What is claimed is:

1. The method of detecting the accretion of frazil ice on water intake grating comprising providing a capacitor including a pair of spaced conductive plates having substantially parallel facing surfaces, immersing said plates in water adjacent water intake grating so that water flowing toward the grating passes between said plates and in contact with said surfaces so that frazil ice may accrete on said surfaces as frazil ice accretes on the grating, and detecting changes in capacitance of said capacitor to indicate the amount of accretion of frazil ice on said surfaces, thereby providing an indication of the amount of accretion of frazil ice on the grating.

2. The method of claim 1 including the step of connecting the capacitor as the capacitive element of an RC oscillator and the further step of connecting the output of the RC oscillator to indicating means responsive to changes in frequency of the output of the RC oscillator.

3. The method of claim 2 wherein the step of connecting the output of the RC oscillator to indicating means comprises connecting the output of the RC oscillator to a plurality of band pass filters, and connecting the output of each of said band pass filters to a light emitting diode.

4. The method of claim 1 indicating the step of connecting the capacitor to a capacitance meter.

5. The method of claim 1 wherein said step of providing a capacitor comprises the step of providing a pair of conductive plates each of which comprises a plate having a plurality of holes formed therethrough.

6. The method of claim 1 wherein said step of providing a capacitor comprises the step of providing a pair of conductive plates each of which is formed of wire mesh.

* * * * *